United States Patent [19]

Lovelace

[11] 3,980,725
[45] Sept. 14, 1976

[54] MESO-1,2,3,4-TETRACHLOROBUTANE PRODUCTION

[75] Inventor: Billy J. Lovelace, Baytown, Tex.

[73] Assignee: Petro-Tex Chemical Corporation, Houston, Tex.

[22] Filed: June 9, 1975

[21] Appl. No.: 585,194

Related U.S. Application Data

[63] Continuation of Ser. No. 484,575, July 1, 1974, abandoned.

[52] U.S. Cl............................................. 260/658 R
[51] Int. Cl.²...................................... C07C 17/04
[58] Field of Search........................ 260/658 R, 660

[56] References Cited
UNITED STATES PATENTS 2,445,729  7/1948  Radcliffe et al. ................. 260/660
3,901,950  8/1975  Richards et al. .................. 260/658
3,932,544  1/1976  Lovelace ............................ 260/658

Primary Examiner—Robert V. Hines
Attorney, Agent, or Firm—N. Elton Dry; Kenneth H. Johnson

[57] ABSTRACT

Meso-1,2,3,4-tetrachlorobutane is produced in an improved liquid phase chlorination process wherein trans-1,4-dichlorobutene-2 is contacted with chlorine in the additional presence of an effective amount of nitric oxide.

17 Claims, No Drawings

MESO-1,2,3,4-TETRACHLOROBUTANE PRODUCTION

This is a continuation of application Ser. No. 484,575, filed July 1, 1974, and now abandoned.

BACKGROUND OF THE INVENTION

1. Field of the Invention

The present invention relates to the production of meso-1,2,3,4-tetrachlorobutane, which compound is of established utility in the production of 2,3-dichlorobutadiene. More particularly, this invention relates to a method for preparing meso-1,2,3,4-tetrachlorobutane from trans-1,4-dichlorobutene-2 in a liquid phase chlorination process.

2. Description of the Prior Art

In preparing meso-1,2,3,4,-tetrachlorobutane from dichlorobutenes in a liquid phase chlorination process, there are produced, in addition to the desired meso-isomer, the dextrorotatory and levorotatory 1,2,3,4-tetrachlorobutanes (the racemic mixture is referred to as dl-isomer) and a proportion of chlorinated materials designated as heavy ends. These heavy ends are generally more highly chlorinated products such as the pentachlorobutanes. The formation of dl-isomer and heavy ends is undesirable in that these materials represent a yield loss and are undesirable contaminants in the desired meso-1,2,3,4-tetrachlorobutane product.

Known methods for preparing meso-1,2,3,4-tetrachlorobutane from dichlorobutenes in a liquid phase chlorination process have been generally unsatisfactory. Non-catalytic processes, such as those disclosed in Japanese Pat. No. 38,802 (1970) and in the Journal of the American Chemical Society 73, 244–6 (1951), require extremely low temperatures of from 0°C. to about −30°C. and are, therefore, generally undesirable economically. Known processes for carrying out the chlorination reaction at moderate temperatures in the range of from about 50°–150°C. involve the use of a catalyst. See, for example, the process disclosed in French Pat. No. 1,401,077 (titanium tetrachloride catalysts), French Pat. No. 1,401,078 (pyridine catalysts), and U.S. Pat. No. 2,445,729 (ferric chloride or antimony pentachloride catalysts). All of these processes are generally unsatisfactory in that there are produced a large proportion of heavy ends material and an undesirably large proportion of the dl-isomer. These catalytic processes are additionally undesirable due to the presence of the metallic catalyst in the reaction product.

SUMMARY OF THE INVENTION

According to the improved process of the instant invention, meso-1,2,3,4-tetrachlorobutane is produced by the liquid phase chlorination of trans-1,4-dichlorobutene-2 in the additional presence of an effective amount of nitric oxide. The presence of nitric oxide suppresses the formation of the dl-isomer and the more highly chlorinated compounds, such as the pentachlorobutanes.

DESCRIPTION OF THE PREFERRED EMBODIMENTS

In accordance with the process of this invention, meso-1,2,3,4-tetrachlorobutane is produced in high yields by the chlorination of certain dichlorobutenes in the additional presence of an effective amount of nitric oxide. The presence of nitric oxide in the reaction zone has been found to enhance the formation of the meso-isomer and to suppress the formation of more highly chlorinated derivatives of the dichlorobutene starting materials, such as pentachlorobutanes.

In the chlorination of trans-1,4-dichlorobutene-1 by conventional processes, not including the addition of nitric oxide, the dl-isomer is produced in appreciable quantities. Typically, a dl-isomer concentration in the chlorination product of from 25 to 40% is common. Moreover, such chlorination processes also result in the production of undesirable higher chlorinated coproducts or heavy ends, often produced in levels ranging from 5 to 10%. However, as the data presented herein illustrates, the chlorination of trans-1,4-dichlorobutene-2, 3,4-dichlorobutene-1 or mixtures thereof in the added presence of nitric oxide greatly suppresses the formation of the dl-isomer and the more highly chlorinated coproducts. In the chlorination process of this invention, at least 90% of the trans-1,4-dichlorobutene-2 is converted to the meso-isomer. Chlorination of 3,4-dichlorobutene-1 in the presence of nitric oxide results in the meso-isomer being formed in proportions near the theoretical maximum, i.e., 50 percent. Also, in the chlorination of either of the above feedstocks or mixtures thereof, the heavy ends formation is suppressed to levels of 2% or less. In a preferred embodiment of this invention wherein nitric oxide is continuously added to the reaction zone during the chlorination of the dichlorobutenes, the heavy ends formation is suppressed to levels considerably less than 1%.

The feedstocks useful in practicing the instant invention are trans-1,4-dichlorobutene-2 and 3,4-dichlorobutene-1. These compounds are generally available in mixtures containing other chlorinated compounds such as, for example, cis-1,4-dichlorobutene-2 and the trichlorobutenes. The presence of these materials is not deleterious to the process of the instant invention; however, concentrations of such compounds should be kept to a minimum inasmuch as they are chlorinated to products other than meso-1,2,3,4-tetrachlorobutane.

The preferred feedstock for practicing this invention is trans-1,4-dichlorobutene-2 since the tetrachloro product from the chlorination of this feedstock is substantially all meso-1,2,3,4-tetrachlorobutane. However, the chlorination of 3,4-dichlorobutene-1 also results in the production of meso-1,2,3,4-tetrachlorobutane; therefore, either trans-1,4-dichlorobutene-2, 3,4-dichlorobutene-1, or mixtures thereof are useful in practicing the instant invention.

The chlorination reaction of the process of this invention is carried out in the reaction zone wherein the liquid dichlorobutene-containing feedstock is contacted with chlorine. The manner by which the contacting is effected can vary depending upon other parameters of the process. In one embodiment of this invention, chlorine is introduced into the gas envelope above the liquid dichlorobutene in a reactor vessel designed for batch chlorinations. The chlorination reaction takes place as the chlorine dissolves into the dichlorobutene reactant in the reactor vessel. The addition of chlorine to the reaction zone is continued until all or a desired amount of the dichlorobutene starting materials have been chlorinated to products. In an alternate embodiment, chlorine is introduced directly into the liquid dichlorobutene reactants, generally by means of a nozzle or plurality of nozzles. Again, the chlorine addition continues until the desired level of chlorination has been effected. In continuous processes, such as where the dichlorobutene reactants are flowing through a tubular reactor, provision can be made for the staged addition of chlorine into the reactor system at a plurality of points.

It is preferred that the manner in which the contacting of the dichlorobutenes and chlorine is effected is such that the chlorine concentration is maintained at as low a concentration as is practicable, since high concentrations of chlorine tend to promote the formation of higher chlorinated derivatives.

In the instant process, chlorine can be introduced into the reaction zone as chlorine gas or as chlorine gas in admixture with a diluent gas which is inert to the reaction environment. Suitable diluent gases include the inert gases such as helium and argon; nitrogen; and saturated lower alkanes such as methane and ethane.

The amount of chlorine utilized in the instant process should be maintained at as low a level as is practicable to effect the desired degree of chlorination. Stoichiometrically, one mole of chlorine is required for each mole of meso-1,2,3,4-tetrachlorobutane to be produced from the dichlorobutene starting materials. Generally, however, a slight excess of chlorine will be required to effect the desired degree of chlorination.

The gist of the instant invention is the carrying out of the chlorination of the dichlorobutenes as herein described in the additional presence of an effective amount of nitric oxide. By effective amount is meant that quantity of nitric oxide necessary to effectively suppress the formation of the undesirable dl-isomer and the higher chlorinated derivatives. An effective amount can be readily determined by one skilled in the art without undue experimentation. The reaction zone configuration and the manner of addition of nitric oxide will, in part, determine what constitutes an effective amount of nitric oxide, as will hereinafter become apparent.

Nitric oxide is provided to the reaction zone so as to be present during the contacting of the dichlorobutenes with chlorine. The nitric oxide preferably is present in the reaction zone both in the liquid dichlorobutene-containing reaction mixture and in the gas envelope of the reaction zone above the liquid reaction mixture. It is introduced into the reaction zone prior to addition of the chlorine, is introduced continuously during the chlorination reaction, or both. Also, the nitric oxide can be added as nitric oxide or in admixture with an inert gas. In one embodiment of the process of this invention, nitric oxide is added to the reaction zone in a gas purge wherein nitric oxide and an inert gas, such as nitrogen, are introduced into the bottom of the reaction zone in the liquid dichlorobutene-containing mixture. The purging action is continued until the reaction zone is free of oxygen and there is sufficient nitric oxide remaining in the reaction zone to effect the desired suppression of the formation of dl-isomer and heavy ends as hereinbefore described. Generally, such a purging action requires from about 2 to about 20 reactor volumes of purging gas and will result in there being from about 0.1 to about 20 mole percent nitric oxide present in the reaction zone, based on the amount of trans-1,4-dichlorobutene-2 present. Thereafter, chlorine is introduced into the reaction zone and the chlorination reaction is begun. In a preferred embodiment of the process of this invention, nitric oxide addition to the reacting zone is continued after the initial purging operation and is maintained throughout the course of the chlorination reaction. Data presented in Example II illustrate the additional advantage obtained by the continuous addition of nitric oxide throughout the course of the chlorination reaction. Whenever nitric oxide, necessary for the practice of this invention, is provided solely by the initial gas purging operation, a nitric oxide concentration of from about 1 to about 20 mole percent, based on the inert gas, is satisfactory. As will be apparent, extremely low concentrations of nitric oxide will require greater volumes of the gas mixture employed in the purging operation to obtain the desired concentration of nitric oxide in the reaction zone and, hence, be unnecessarily wasteful of the inert purging gas, whereas extremely high concentrations of nitric oxide may be economically prohibitive. Preferably, the reaction system is purged with an inert gas until substantially free of oxygen and then the purging operation is continued for a suitable period with the additional presence of nitric oxide in the purging gas. In practicing a preferred embodiment of this invention wherein nitric oxide is added continuously throughout the course of the chlorination reaction, nitric oxide addition rates of from about 0.1 to about 10% by volume based on the chlorine addition rate is satisfactory, with a nitric oxide addition rate of from about 0.5 to about 5% being preferred.

It is desirable that there be provided in the reaction zone suitable means for agitating the liquid reaction mass to facilitate the contact of the chlorine or chlorine-containing gas with the dichlorobutenes. Agitation of the reaction mixture also insures that there is a good distribution of chlorine throughout the reaction mixture and that undesirably high chlorine concentrations are thereby avoided. Any number of agitator means are suitable, as will be apparent to one skilled in the art. For example, it has been found useful to employ propeller driven agitators, turbine blades, orifice mixing devices, inert gas spargers, and various baffle arrangements in the reaction zone.

The temperature at which the chlorination reaction of this invention is carried out is not critical and can vary over wide limits. It has been found that satisfactory results are obtained whenever the chlorination reaction as described herein is carried out at temperatures of from about 25° to about 150°C. A preferred temperature range for conducting the chlorination of 1,4-trans-dichlorobutene-2 is from about 50° to about 100°C. The pressure at which the process of this invention is conducted is, likewise, not critical and can vary over rather wide limits. As a general proposition, the higher the reaction pressure selected, the higher the rate at which the chlorine is dissolved into the liquid reaction medium. Suitable reaction pressures can include subatmospheric pressure, atmospheric pressure or superatmospheric pressure. Generally, however, subatmospheric pressure is avoided because of the concomitant problems associated with the leakage of oxygen into the reaction system. Preferred reaction pressures are within the range of about 15 psia to about 100 psia, with reaction pressures of from about 15 psia to about 50 psia being especially preferred.

Although the process of the instant invention can be carried out in the absence of any solvent, it is equivalently useful to provide a solvent for the reactants. Suitable solvents generally include halogenated solvents such as methylene chloride, chloroform, carbon tetrachloride, and certain halogenated aromatic solvents such as chlorobenzene. Whenever a solvent is employed in the process of the instant invention, the amount is not critical and can vary. Solvent concentrations of from about 10 to about 90 wt. % are satisfactory, with concentrations of from about 25 to about 75 wt. % being preferred.

Subsequent to the reaction, the unreacted chlorine is generally removed from the crude product mixture and the desired meso-1,2,3,4-tetrachlorobutane product is thereafter recovered by conventional means, such as by fractional distillation, selective extraction, fractional crystallization and the like. Unreacted dichlorobutenes are recovered and recycled for further reaction according to the process of this invention. The meso-1,2,3,4-tetrachlorobutane is generally recovered in high purity from the crude product containing both the dl- and meso-isomers by conventional fractional crystallization techniques. The small proportion of trichloro compounds, generally present in the reaction mixture, may be recovered as a separate product.

As mentioned previously, meso-1,2,3,4-tetrachlorobutane is a compound of established utility. The meso-1,2,3,4-tetrachlorobutane is dehydrochlorinated to 2,3-dichlorobutadiene which is useful either alone or as a comonomer with chloroprene in the production of specialty rubber compositions.

To further illustrate the process of this invention, the following examples are provided. It should be understood that the details thereof are not to be regarded as limitations.

EXAMPLE I

This Example illustrates the effect of carrying out the chlorination of trans-1,4-dichlorobutene in the added presence of nitric oxide. In each of the three runs reported in Table I, the feedstock was charged into a 1-liter, 3-necked flask equipped with a water jacket for cooling and an agitator means. The reaction flask in each case was then purged of oxygen using a stream of nitrogen gas. In Run A, only nitrogen was used to purge the reaction system, whereas in Runs B and C, the nitrogen gas additionally contained about 10 mol percent nitric oxide. In each run, the chlorination was effected by maintaining the liquid reaction mixture under agitation and introducing chlorine into the gas space above the reaction mixture. The chlorine was dissolved into the dichlorobutene (DCB) liquid wherein the chlorination reaction was effected. The rate at which chlorine was introduced into the reaction flask was maintained at a rate which resulted in the indicated chlorination rates. The temperature of the reaction mixture was maintained at approximately 70°C. by adjustment of the cooling water flow through the water jacket surrounding the reaction flask. The end of the chlorination reaction was determined to be that point at which the indicated temperature of the reaction mixture began to decrease. The data for the three runs are presented in the following Table I.

Table I

| Run | A | B | C |
|---|---|---|---|
| Feed Composition | | | |
| 3,4-dichlorobutene-1 | 2.2 | 2.2 | 2.2 |
| cis-1,4-dichlorobutene-2 | 4.1 | 4.7 | 4.1 |
| trans-1,4-dichlorobutene-2 | 93.3 | 92.6 | 93.3 |
| Feed Charged, g. | 284 | 307 | 314 |
| Chlorination Temp., °C. | 70 | 70 | 70 |
| Chlorination rate, | | | |
| Mol DCB chlorinated | | | |

Table I-continued

| Run | A | B | C |
|---|---|---|---|
| hr. | 1.5 | 1.5 | 1.3 |
| N₂/NO Purge | No* | Yes** | Yes** |
| Product Composition | | | |
| Unreacted DCB | 0.4 | — | 0.2 |
| Light ends | 1.2 | 6.5 | 7.4 |
| dl-1,2,3,4-tetrachlorobutane | 33.2 | 6.9 | 6.3 |
| meso-1,2,3,4-tetrachlorobutane | 56.8 | 84.9 | 85.5 |
| Heavy ends | 8.1 | 1.6 | 0.5 |

*Nitrogen only at 1100 ml/min sparged through reactor for 5 minutes.
**1000 ml/min nitrogen and 100 ml/min nitric oxide sparged through reactor for 5 minutes.

At the end of the reaction period, the product was worked up as follows. A heating medium was substituted for the cooling water in the water jacket and the temperature of the reaction flask contents was maintained at 70°C. The reaction flask was then purged with nitrogen to degas the system of the residual chlorine. Throughout the purging, the contents of the reaction flask were stirred to liberate any entrained chlorine. A sample from the reaction flask was dissolved in dichloromethane and analyzed by gas chromatographic techniques to yield the above analyses. The remaining contents of the reaction flask were then diluted with approximately one-half its volume of isopropyl alcohol. The mixture was then stirred rapidly and allowed to cool to 70°–75°C. At this temperature, crystallization of the meso-1,2,3,4-tetrachlorobutane was effected. The crystals, after filtering, washing, and drying analyzed 99+ wt. % meso-1,2,3,4-tetrachlorobutane.

From the above data in Table I, it is apparent that carrying out the chlorination in the additional presence of nitric oxide has a dramatic effect upon the isomer distribution of the tetrachlorobutanes produced, as well as on the proportion of heavy ends produced.

EXAMPLE II

This Example illustrates an alternate embodiment of the process of this invention, wherein nitric oxide is added continuously throughout the chlorination reaction. In both of the runs which are tabulated in Table II, the reaction flasks were purged of oxygen by sparging the reaction flask containing the dichlorobutene feedstock with a mixture of nitrogen and nitric oxide. Thereafter, the chlorine was introduced into the dichlorobutene reaction mixture via a 4-mm. nozzle positioned below the liquid level of the reaction flask to effect the chlorination. In Run D, the chlorination reaction was carried out with nitric oxide being added continuously to the reactor vessel along with the chlorine. In Run E, the chlorination was carried out without the continuous addition of nitric oxide during the chlorination. The data from these two runs are listed in the following Table II.

Table II

| Run | D | E |
|---|---|---|
| Feed Composition | | |
| 3,4-dichlorobutene-1 | 2.2 | 2.5 |
| cis-1,4-dichlorobutene-2 | 4.1 | 5.4 |
| trans-1,4-dichlorobutene-2 | 93.3 | 91.3 |
| Feed charged, g. | 252 | 1022 |
| Chlorination Temp., °C. | 70 | 70 |
| Chlorination rate, | | |
| Mol DCB chlorinated | | |
| hr. | 1.0 | 0.8 |
| N₂/NO Gas Purge* | Yes | Yes |

Table II-continued

| Run | D | E |
|---|---|---|
| Continuous NO addition** | Yes | No |
| Product Composition | | |
| Unreacted DCB | 0.8 | — |
| Light ends | 7.6 | 7.3 |
| dl-1,2,3,4-tetrachlorobutane | 6.4 | 10.3 |
| meso-1,2,3,4-tetrachlorobutane | 84.8 | 80.2 |
| Heavy ends | 0.2 | 2.2 |

*1000 ml/min nitrogen and 100 ml/min nitric oxide sparged through reaction zone for 5 minutes.
**Approximately 10 ml/min.

From the above, it is apparent that the effect of continuously adding nitric oxide throughout the chlorination reaction even further reduces the production of the heavy ends materials.

From the foregoing description and examples of this invention, those of ordinary skill in the art may make many modifications and variations therefrom without departing from the scope of the invention as hereinafter claimed.

I claim:

1. In a process for the production of meso-1,2,3,4-tetrachlorobutane by contacting in a reaction zone trans-1,4-dichlorobutene-2 in the liquid phase with chlorine at a temperature of from about 25°C. to about 150°C. in the substantial absence of oxygen, the improvement which comprises:
   effecting said contacting of trans-1,4-dichlorobutene-2 and chlorine in the presence of an effective amount of nitric oxide.

2. The process according to claim 1 wherein nitric oxide is added to the reaction zone in an amount of from about 0.1 to about 20 mole percent based on the trans-1,4-dichlorobutene-2.

3. The process according to claim 2 wherein the nitric oxide is introduced into the reaction zone prior to said contacting of the trans-1,4-dichlorobutene-2 and the chlorine.

4. The process according to claim 2 wherein the nitric oxide is introduced into the reaction zone during said contacting of the trans-1,4-dichlorobutene-2 and the chlorine.

5. The process according to claim 3 wherein the nitric oxide is introduced into the liquid trans-1,4-dichlorobutene containing reactant in admixture with an inert purge gas selected from the group of nitrogen, argon and methane, the nitric oxide being present in an amount of from about 1 to about 20 mole percent based on the inert gas and said inert gas-nitric oxide mixture being employed in an amount of from about 2 to about 20 volumes, based on the volume of the reaction zone.

6. The process according to claim 5 wherein the nitric oxide is further continuously introduced during the contacting of the trans-1,4-dichlorobutene-2 and the chlorine in an amount of from about 0.1 to about 10 volume percent based on the volume of chlorine.

7. The process according to claim 6 wherein said contacting is effected by introducing the chlorine into the gas space of the reaction zone containing the liquid trans-1,4-dichlorobutene-2 whereby the chlorine dissolves into the trans-1,4-dichlorobutene-2 at the liquid-gas interface in the reaction zone.

8. The process according to claim 6 wherein said contacting is effected by introducing the chlorine into the liquid trans-1,4-dichlorobutene-2-containing reaction mixture.

9. A process for the production of meso-1, 2, 3, 4-tetrachlorobutane by contacting in a reaction zone trans-1, 4-dichlorobutene-2 in the liquid phase with chlorine at a temperature from about 50° to 100°C. in the substantial absence of oxygen said contacting being effected in the presence of an effective amount of nitric oxide.

10. The process according to claim 9 wherein the contacting of trans-1,4-dichlorobutene-2 and chlorine is effected in the absence of catalysts.

11. The process according to claim 9 wherein nitric oxide is continuously introduced during the contacting of trans-1, 4-dichlorobutene-2 and chlorine.

12. The process according to claim 11 wherein nitric oxide is added at rates of from about 0.1 to about 10% by volume based on the chlorine addition rate.

13. The process according to claim 12 wherein the rates of nitric oxide addition are from about 0.5 to about 5%.

14. The process according to claim 9 wherein nitric oxide is introduced into the reaction zone prior to said contacting of trans-1,4-dichlorobutene-2 and the chlorine.

15. The process according to claim 14 wherein said nitric oxide is introduced into said reaction zone prior to said contacting, in admixture with an inert purge gas.

16. The process according to claim 15 wherein said inert purge and nitric oxide mixture are employed in an amount of from about 2 to about 20 volumes, based on the volume of the reaction zone and said nitric oxide is present in an amount of from about 1 to 20 mole percent based on the inert purge gas.

17. The process according to claim 16 wherein nitric oxide is further continuously introduced into said reaction zone during the contacting of the trans-1, 4-dichlorobutene-2 and chlorine in an amount of from about 0.1 to about 10 volume percent based on the volume of chlorine.

* * * * *